United States Patent

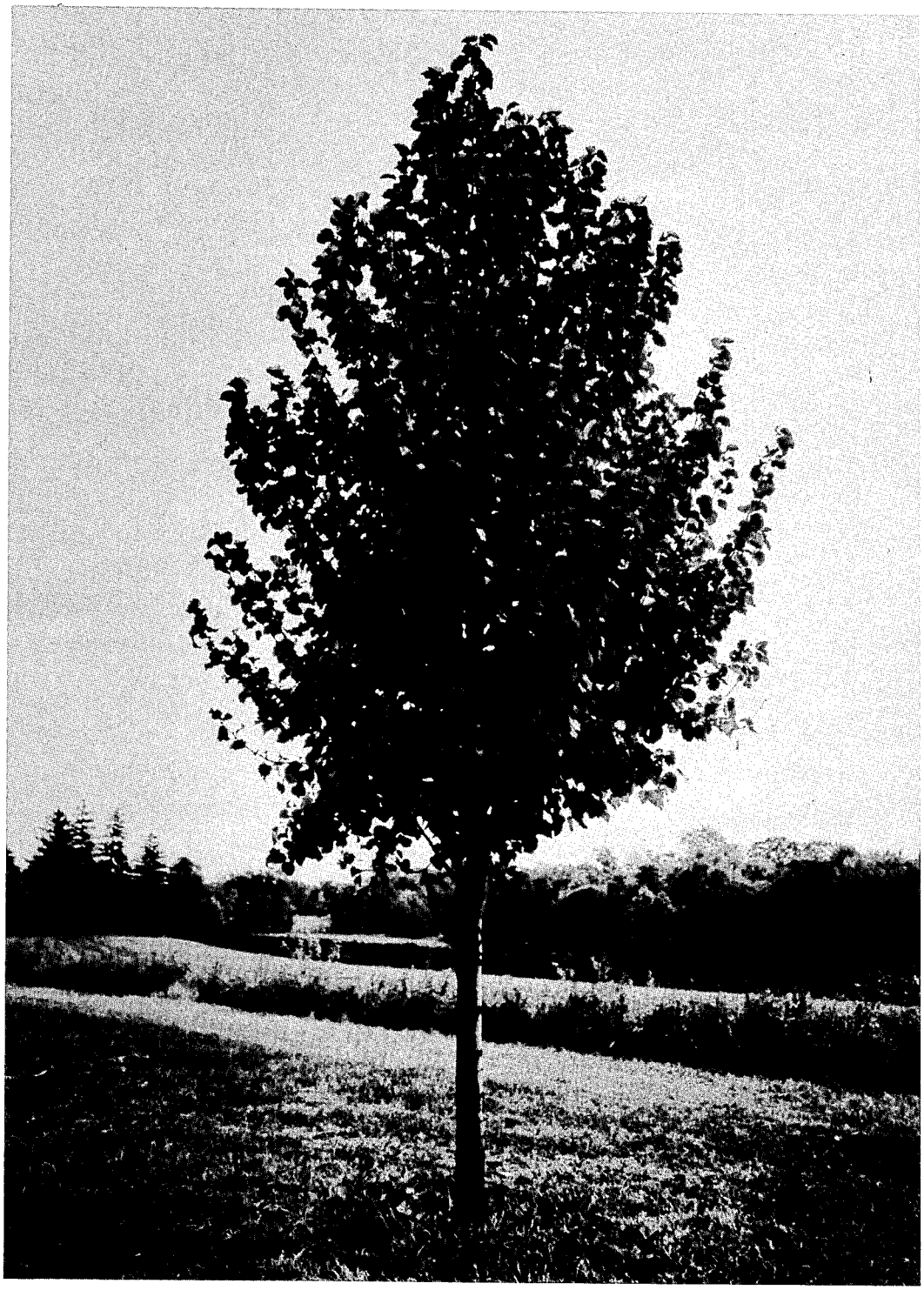

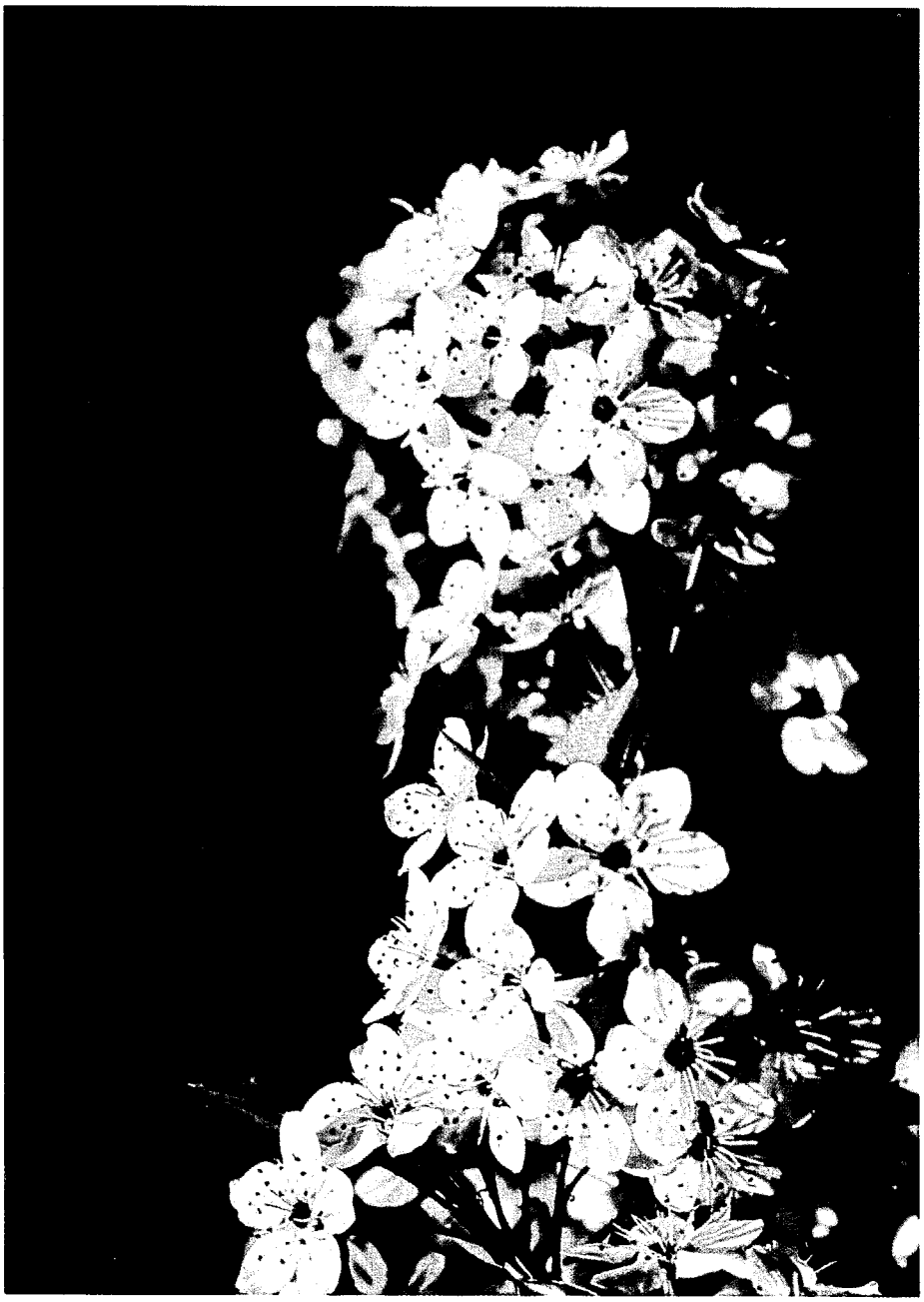

Plant Pat. 3,815

Patented Dec. 16, 1975

1

3,815

FLOWERING PEAR TREE

William Flemer III, Princeton, N.J., assignor to Treesearch, Kingston, N.J.

Filed July 16, 1974, Ser. No. 488,960

Int. Cl. A01h 5/03

U.S. Cl. Plt.—36 1 Claim

The present invention relates to a new and distinct variety of flowering pear tree of the species botanically known as *Pyrus calleryana,* which was discovered by me as a cultivated open-pollinated seedling mutation of the *Pyrus calleryana* variety known as "Bradford" (unpatented).

At the time of my discovery, a block of seedlings of the "Bradford" variety were being grown under my direction and supervision in my nursery located in South Brunswick Township, N.J. In one row of these trees, my attention was attracted to one particular seedling which differed materially from the others, particularly in respect to its dense, robust and pyramidal habit of growth and its large, glossy foliage. I carefully preserved this seedling and kept it under close observation. In due course, I asexually propagated the same by bud-grafting, as performed by me in my nursery aforesaid.

Continued observation of the original seedling and the progeny derived therefrom as aforementioned, confirmed that its pyramidal form and large, glossy foliage were established features thereof, along with other distinctive features which I observed during my observations and tests extending over a prolonged period of years. I am accordingly convinced that my new seedling represents a new and improved variety of flowering pear tree, as particularly evidenced by the following unique combination of principal characteristics which are outstanding therein and which distinguish it from the "Bradford" variety, as well as from all other varieties of flowering pear trees of which I am aware:

(1) A dense, robust and pyramidal habit of growth;
(2) Large, glossy foliage;
(3) Late flowering and leafing out habits, both of which are about ten days later than the variety "Bradford";
(4) Cessation of growth and ripening up of the wood earlier in the fall than the variety "Bradford"; and
(5) Greater hardiness than the variety "Bradford," as evidenced by its ability to survive winters in central Vermont which killed "Brawford" outright in the same plantings.

Asexual reproduction of my new variety by bud-grafting, as performed by me in my nursery located in South Brunswick Township, N.J. shows that the foregoing characteristics and distinctions come true and are established and transmitted through succeeding propagations.

The accompanying drawings show a typical specimen tree of my new variety depicting its dense and pyramidal habit of growth, as well as its typical flowers.

The following is a detailed description of my new variety of flowering pear tree, with color terminology in accordance with the Nickerson Color Fan, published by Munsell Color Company, Inc., of Baltimore, Md.:

Parentage: On open-pollinated seedling mutation.
*Seed parent.*—*Pyrus Calleryana* "Bradford."
*Pollen parent.*—Unknown.
Propagation: Holds its distinguishing characteristics through succeeding propagations by bud-grafting.
Locality where grown and observed: South Brunswick Township, N.J.
Tree: Small; upright; pyramidal; dense; hardy.

2

*Trunk.*—Stocky; rough.
*Branches.*—Stocky; smooth. Color—Brownish Gray, Hue 10YR3/1. Lenticels—Sparse; small.
Foliage: Leaves—Very thick; abundant; glossy.
Size.—Length—About 11 cm. as compared to 8.5 to 9.5 cm. for "Bradford" when grown in adjacent rows under identical conditions. Width—About 6 cm.
*Shape.*—Oval-acuminate.
*Color.*—Upper surface—Moderate Olive Green. Hue 5GY 4/3. Lower surface—Moderate Yellow Green, Hue 5GY 5/6.
*Margin.*—Minutely crenate.
*Petiole.*—Medium length (about 3 cm. long).
*Glands.*—None.
*Stipules.*—Very narrow; about 2 cm. long.
Flower buds:
*Hardiness.*—Hardy in zones 4 and 5; no damage to buds in winters in these zones when most "Bradford" trees freeze back or are killed outright.
*Size.*—About 0.5 cm. long; about 0.25 cm. wide.
*Shape.*—Pointed.
*Color.*—Strong Brown, Hue 5YR 4/5.
Flowers:
*Bloom dates.*—First bloom—About April 15 in New Jersey. Full bloom—About April 20 in New Jersey.
*Quantity.*—Abundant.
*Size.*—Large (from about 2.0 to 2.2 cm. in diameter).
Petalage:
*Number of petals.*—5.
*Shape of petals.*—Oval.
*Size of petals.*—Length—About 1.5 cm. Width—About 1.2 cm.
*Color.*—White, with Vivid Yellow stamens, Hue 2.5Y 8/12.
Fruits:
*Borne.*—September to November.
*Abundance.*—Not abundant; self-sterile; not produced unless planted near another clone.
*Form.*—Egg-shaped.
*Size.*—Length—From about 1 to 1.2 cm. long. Width—From about 0.8 to 1 cm. wide. Color—Moderate Brown, Hue 7.5YR 4/5.

GENERAL OBSERVATIONS

In comparison with the parent variety "Bradford," my new variety is primarily and consistently distinguished therefrom by a more dense and more robust growth habit, larger foliage, later flowering and leafing out habits and greater winter-hardiness as the result of earlier cessation of growth and earlier ripening and hardening of the wood in the fall when grown under the same conditions in New Jersey, Vermont and Oregon. In the Vermont tests, where the climate is more severe than in New Jersey, eleven test trees of my new variety were observed in comparison with "Bradford" trees for over five years, and the "Bradford" were less hardy and many failed to survive some winters, while those of my new variety grown in the same planting under identical conditions all survived without damage and without injury to the buds, due to their more determinate growth habit of growing during the summer months, but stopping growth earlier as fall approached, usually in the month of September, to allow hardening up sufficiently to escape injury during the winter season.

This same improved hardiness of my new variety has also been confirmed in Oregon where "Bradford" continues to grow so late in the fall that when cold weather arrives, the trees freeze back from the sensitive terminals and usually are killed outright.

In comparison with the variety "Chanticleer" (Plant Pat. No. 2,489), my new variety is primarily a much more robust and denser tree. This is largely due to the fact that it has twigs that are at least twice as thick as those of "Chanticleer," and the foliage of the new variety is thicker and more leathery. The twigs of my new variety are darker in color (Moderate Brown, Hue 5YR 3/3) whereas the twigs of "Chanticleer" are much paler (Brownish Orange, Hue 5YR 5/8). The flowers of my new variety are much larger (from 2 to 2.2 cm. in diameter) than those of "Chanticleer" which usually range from 1.5 to 1.6 cm. in diameter. The leaves of my new variety are longer (from 10.5 to 11.5 cm. long) than the leaves of both "Bradford" (8.5 to 9.5 cm. long) and "Chanticleer" (7.0 to 8.0 cm. long).

The foregoing comparisons were made from numerous test trees that have been grown under the exact same nursery conditions in various regions of the United States and which have been closely observed over periods ranging from at least 5 to 10 years.

I claim:

1. A new and distinct variety of flowering pear tree of the species botanically known as *Pyrus calleryana*, substantially as herein shown and described, characterized particularly as to novelty by the unique combination of a dense, robust and pyramidal habit of growth; large, glossy foliage; late flowering and leafing out habits, both of which are about ten days later than the variety "Bradford"; cessation of growth and ripening up of the wood earlier in the fall than the variety "Bradford"; and greater hardiness than the variety "Bradford," as evidenced by its ability to survive winters in central Vermont which killed "Bradford" outright in the same plantings.

References Cited

UNITED STATES PATENTS

P.P. 2,489 3/1965 Scanlon ---------- Plants—36

ROBERT E. BAGWILL, Primary Examiner